United States Patent [19] [11] 4,114,669
Bishop [45] Sep. 19, 1978

[54] STERILE PORT STRUCTURE

[76] Inventor: Marilyn Bishop, One N. 341 Indian Knoll Rd., West Chicago, Ill. 60185

[21] Appl. No.: 656,470

[22] Filed: Feb. 9, 1976

Related U.S. Application Data

[62] Division of Ser. No. 479,755, Jun. 17, 1974, Pat. No. 3,968,195.

[51] Int. Cl.2 .............................................. F16L 55/10

[52] U.S. Cl. .......................................... 150/8; 138/89; 138/89.3

[58] Field of Search .......................... 138/89, 89.3, 93; 150/8

[56] References Cited

U.S. PATENT DOCUMENTS

| | | | |
|---|---|---|---|
| 2,229,379 | 1/1944 | Keefe | 138/89.3 |
| 2,424,802 | 7/1947 | Crowley | 138/89.3 |
| 2,588,306 | 3/1952 | Taylor | 138/89 |
| 2,712,384 | 7/1955 | Corneil | 138/89 |
| 2,901,161 | 8/1959 | Henchert | 138/89 |
| 3,201,136 | 8/1965 | Harrison | 138/89 |
| 3,992,570 | 11/1976 | Beinhaur | 138/89 |
| 4,021,907 | 5/1977 | Zondag | 138/89 |

*Primary Examiner*—Ro E. Hart
*Attorney, Agent, or Firm*—Jerold A. Jacover

[57] ABSTRACT

A port structure for passing sterile fluids or other biological material, and a method for making the same is disclosed. The port structure includes a flexible sleeve having a rigid thermoplastic tube secured therein. The outer surface of the sleeve has greater thermoplastic properties than the inner surface, enabling the sleeve to be heat sealed to the fluid passage means without sealing off the inner surface. The rigid tube has a free end extending outside the sleeve, having a thermoplastic diaphragm which seals off the free end. When a sterile connection between two fluid passage means incorporating the port structure is desired, the free ends of each rigid tube are aligned and softened, and each thermoplastic diaphragm is opened. The free ends of the rigid tubes are then brought into contact and held in position under a slight pressure while the thermoplastic tubes cool and solidify, thereby creating a permanent connection.

5 Claims, 7 Drawing Figures

12c
17c
12a
17a
10
11
17b
12b 19
23
21
20

22
17
16
14
13
12
10

10a
29a
19b
20b
16b
10b
16a
17a
20a
19a
17b
29b 20a
20b
16b
10a
16a
17a
17b
10b
30

10a
16a
16b
10b
17a
20a
20b
17b 14
13
16
21
17
20
22
18

19
21
13
20
18
22
16
17
14

STERILE PORT STRUCTURE

This application is a division of United States application Ser. No. 479,755 filed on June 17, 1974 by the same inventor named herein now U.S. Pat. No. 3,968,195.

BACKGROUND OF THE INVENTION

This invention relates to a port structure used with containers for holding or passing sterile fluids or biological materials, and a method for making the same.

At the present time there are numerous medical and scientific practices which require the sterile transfer of fluids or other biological materials from one container to another. The state of the art is such, however, that no true sterile method for joining separate containers to facilitate the sterile transfer of fluids is available. Thus, where a sterile transfer from one container to another is required, it is often accomplished by prejoining the containers together and then sterilizing the entire assembly. This method is not entirely satisfactory because it necessitates the handling of cumbersome prejoined units, and involves additional costs associated with prejoined containers.

When prejoined units are impracticable, separate containers are generally connected by means of a sterile transfer set. Such a transfer set includes a pair of plastic couplers which are adapted to pierce and penetrate the corresponding containers to be joined. Once the transfer set is removed from its sterilized package, however, the plastic couplers are susceptible to contamination from airborne bacteria. As a result, a sterile connection cannot be assured. Moreover, as a general rule, a sterile transfer set can be correctly used only by persons who have had proper training.

The method and apparatus of the invention achieves a true sterile connection which can be accomplished with only a minimal amount of training and skill. More particularly, the apparatus of the invention includes a port structure comprising a flexible thermoplastic sleeve heat sealed to any fluid passage means such as a container, and a thermoplastic tube secured to the sleeve to form an extension thereof. Though this thermoplastic tube is hereinafter characterized as "rigid," that term, as used herein, should not be construed synonymously with "brittle," but is intended to describe a structure having sufficient stiffness to maintain its shape under its own weight. The rigid tube has a free end extending beyond the sleeve which is adapted to be joined to the free end of a second rigid tube extending from a sleeve. This second rigid tube and second flexible sleeve comprise a second port structure secured to a second container. Preferably secured near the outer end of each rigid tube is a thermoplastic diaphragm which initially seals off each free end and is subsequently melted open just prior to joining the rigid tubes together in order to effect a sterile connection between the first and second containers.

Sterile joinder of the two containers is achieved by bringing the first and second rigid tubes into alignment and softening the facing ends thereof, preferably through the application of heat. During this heating process, the thermoplastic diaphragms which previously sealed off each rigid tube are softened, and ultimately melted open. The facing ends of the rigid tubes are then brought into contact and hardened preferably by holding the ends together under a slight pressure while the thermoplastic tubes cool and solidify. Upon solidification, a a permanent connection is formed thereby permitting fluid transfer between the two containers.

OBJECTS OF THE INVENTION AND A BRIEF DESCRIPTION OF THE DRAWINGS

It is a primary object of this invention to provide an improved port structure for use with fluid passage means adapted to carry or pass sterile fluid or other biological material.

It is another object of this invention to provide a method for making a sterile connection between two means for passing fluid.

It is a further object of this invention to provide a method for making an improved port structure for use with fluid passage means.

It is still another object of this invention to provide an improved port structure for use with fluid passage means having a flexible thermoplastic sleeve and a rigid thermoplastic tube secured therein.

A feature of this invention provides a method for making a sterile connection between two means for passing fluid requiring minimal skill or training.

Other objects, features and advantages of this invention will become apparent upon reading the following description in conjunction with the accompanying drawings in which.

DETAILED DESCRIPTION OF THE INVENTION

Figure 1:
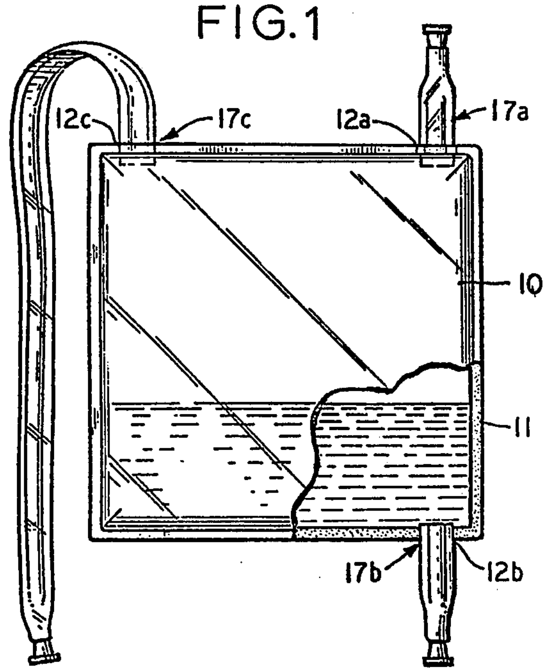
FIG. 1 is a front view of a container incorporating the port structure of the invention.

Referring now to FIG. 1, means for holding or passing fluid or biological material such as a container 10, is shown. Container 10 is preferably formed entirely of two layers of thermoplastic material, heat sealed together to form a watertight seam 11. Disposed about seam 11 of container 10 are any number of ports, three of which are shown in FIG. 1 at **12*a*, 12*b* and 12*c*. Adapted to fit each of ports 12*a*, 12*b* and 12*c* are a corresponding number of port structures represented specifically by reference numerals 17*a*, 17*b* and 17*c*, and represented in general by reference numeral 17**.

Figure 2:
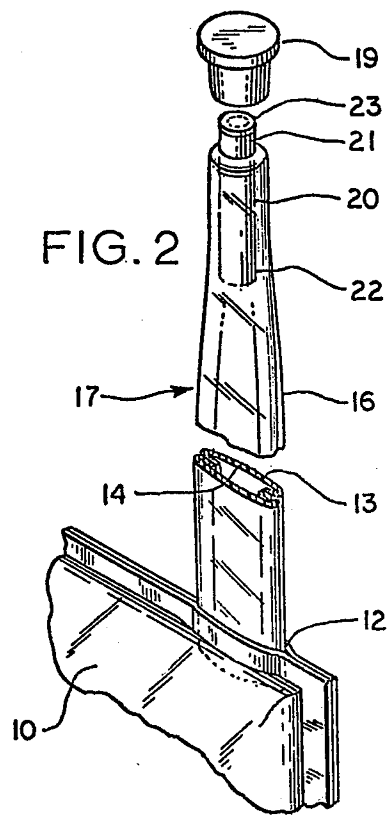
FIG. 2 is an enlarged, fragmented view, taken in perspective of the port structure of the invention.

Port structure 17, shown in greater detail in FIG. 2, is comprised of a flexible thermoplastic sleeve 16 having an inside surface 14 and an outside surface 13 sealed into a container 10 at port 12. Outside surface 13 has greater thermoplastic properties than inside surface 14. This may be accomplished by utilizing a two-ply sleeve, or by coating either inside surface 14 or outside surface 13 with a substance adapted to respectively decrease or increase the thermoplastic properties. In the preferred embodiment, outside surface 13 is a heat sealable coating applied to a polyester film which forms inside surface 14, whereby the application of heat to sleeve 16 enables outside surface 13 to adhere to the inside of container 10 without sealing off inner surface 14.

Port structure 17 further includes a rigid tube 20 having one end 22 secured inside sleeve 16 and a free end 21 extending outside sleeve 16. A thin thermoplastic diaphragm 23 seals off rigid tube 20 at free end 21. Diaphragm 23 has relatively great thermoplastic properties, whereby the application of heat at free end 21 of rigid tube 20 causes the softening and opening of diaphragm 23. A cap 19, adapted to be removably secured over free end 21, is used to protect diaphragm 23 from exposure to gross contamination and accidental puncture. Such a puncture could, of course, expose the interior of port structure 17 to airborne bacteria, thereby making the fluid inside container 10 susceptible to contamination. As a result, it is preferred that cap 19 not be removed until a sterile connection is ready to be made.

Figure 3:
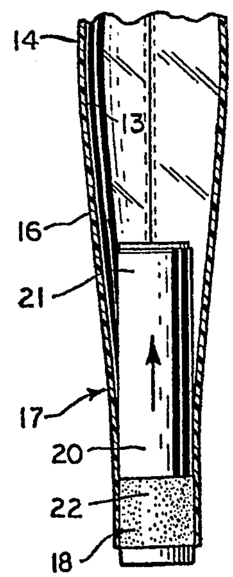
FIGS. 3 and 4 are enlarged front views of the port structure of the invention, illustrating the manner in which the port structure is made; and FIGS. **5*a*, 5*b* and 5*c*** show two port structures of the invention, and illustrate the method by which a sterile connection between two containers is made.
Figure 4:
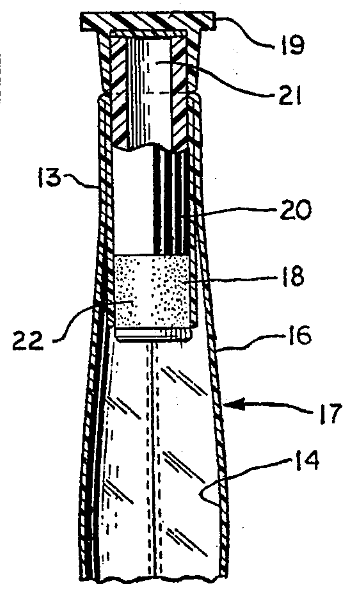

FIGS. 3 and 4 illustrate the manner in which port structure 17 is made. More particularly, flexible sleeve 16 is shown in FIG. 3 with inside surface 14 temporarily on the outside, and outside surface 13 temporarily on the inside. Thus, surface 14 may sometimes be referred to herein as a temporary outside surface, and likewise, surface 13 may sometimes be referred to herein as a temporary inside surface.

Still referring to FIG. 3, the free end 21 of rigid tube 20 is inserted deep into sleeve 16 so that end 22 is also captivated thereby. End 22 is adapted to adhere to the temporary inside surface (surface 13) of sleeve 16 to form a watertight seal 18. The remaining length of sleeve 16, however, is not sealed to rigid tube 20 but is free to move relative thereto.

To complete the construction of port structure 17, sleeve 16 is turned inside out by doubling it back over free end 21 of rigid tube 20, forming a fold which overlaps seal 18. As shown in FIG. 4, free end 21 will then extend outside sleeve 16. Further, the temporary inside surface (surface 13) of sleeve 16 now appears on the outside, and the temporary outside surface (surface 14) now appears on the inside. As shown in FIG. 2, the lower open end of sleeve 16 is then secured inside container 10 to form a watertight connection at port 12.

Figure 5A:
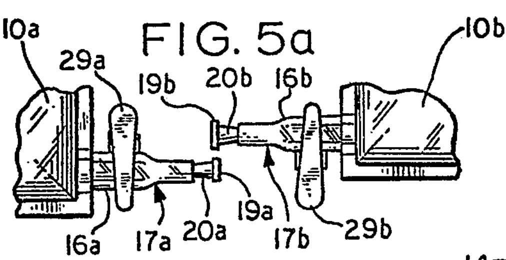

The manner in which a sterile connection is made between any two fluid passage means having a port structure having an end configuration consisting of a rigid tube sealed off by a thermoplastic diaphragm can now be explained by referring to FIGS. **5*a*, 5*b* and 5*c*. FIG. 5*a* shows two port structures identified, respectively, by reference numerals 17*a* and 17*b*. Port structures 17*a* and 17*b* are corresponding fluid passage means represented, for exemplary purposes only as a pair of containers 10*a* and 10*b*. Port structures 17*a* and 17*b* are respectively comprised of flexible sleeves 16*a* and 16*b*, and rigid tubes 20*a* and 20*b*. Secured near the end of each rigid tube, at the free end thereof, is a thin thermoplastic diaphragm such as the one represented by reference numeral 23 in FIG. 2. For reasons explained above, the free end of each rigid tube is protected by caps identified, respectively, by reference numerals 19*a* and 19*b*. So that fluid from neither containers 10*a* nor 10*b* is prematurely passed, a pair of clamps 29*a* and 29*b* is used to close off port structures 17*a* and 17*b***, respectively. Said clamping action is, of course, most easily accomplished by clamping across the flexible sleeve rather than across the rigid tube.

Figure 5B:
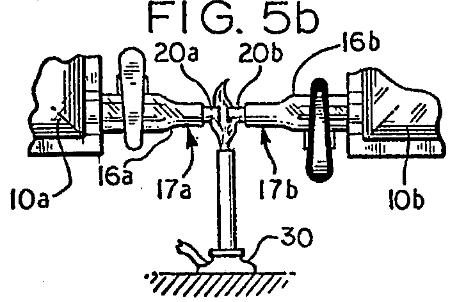
Figure 5C:
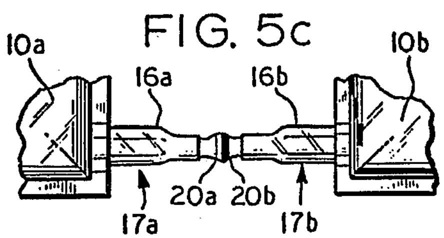

To make the sterile connection, caps **19*a* and 19*b* are removed, and rigid tubes 20*a* and 20*b* are aligned as shown in FIG. 5*b*. Heat is then applied to the free end of rigid tubes 20*a* and 20*b* in any suitable manner, such as through use of a Bunsen burner 30. The heat from Bunsen burner 30 causes the free ends of rigid tubes 20*a* and 20*b* to soften until their respective thermoplastic diaphragms melt open. Thereupon, the tube ends are brought into contact and held in position, preferably under slight pressure, while the rigid tubes cool and solidify to form a permanent connection. Thus, upon removal of clamps 29*a* and 29*b*, a fluid passage path between containers 10*a* and 10*b* is completed as shown in FIG. 5*c***.

Since the thin thermoplastic diaphragms 23 near the end of rigid tubes **20*a* and 20*b* are not opened until the free ends thereof are aligned, softened and ready to be contacted, the interior of the rigid tubes is susceptible to airborne bacteria only for a minute period of time. Even during this period of time, however, the free ends of the rigid tubes are subjected to the sterilizing effects of a high temperature such as the open flame from Bunsen burner 30**, thereby assuring a sterile connection. Moreover, since only the simplest manual skills are needed to heat the free ends of the rigid tubes and bring them together, this sterile connection can be made by people having a most minimal amount of training.

Though the embodiment of the invention herein disclosed is preferred, it will be apparent to those skilled in the art that alternatives, variations, and modifications can be devised without departing from the true scope of the invention. It is intended, however, that the appended claims encompass all such alternatives, variations and modifications.

I claim:

1. A port structure for use with fluid passage means comprising:

a flexible sleeve having an inner surface, and an outer surface having greater thermoplastic properties than said inner surface; and a rigid tube secured to said sleeve having a free end extending beyond said sleeve, whereby said outer surface of said sleeve can be heat sealed to said fluid passage means without sealing off said inner surface.

2. The port structure set forth in claim 1 further includes a thermoplastic diaphragm secured near said free end of said rigid tube for sealing off said free end.

3. The port structure set forth in claim 1 further includes a cap removably securable to said free end of said rigid tube.

4. A port structure for use with fluid passage means comprising:

a flexible sleeve having an inner surface, and an outer surface having greater thermoplastic properties than said inner surface; said sleeve further having a fold wherein a portion of said outer surface is doubled back inside said sleeve;

a rigid tube, secured inside said sleeve at said fold, having a free end extending outside said sleeve; and a thermoplastic diaphragm secured inside near said free end of said rigid tube for sealing off said free end.

5. The port structure set forth in claim 4 further includes a cap removably securable to said free end of said rigid tube.

* * * * *